United States Patent [19]

Resler

[11] Patent Number: 5,650,138

[45] Date of Patent: Jul. 22, 1997

[54] COMPOSITION AND METHOD FOR APPLYING PROTECTIVE COATING ON A NAIL SURFACE

[76] Inventor: Renee Resler, 3046 E. Marlette, Phoenix, Ariz. 85016

[21] Appl. No.: 404,374

[22] Filed: Mar. 15, 1995

[51] Int. Cl.⁶ .................. A61K 7/04; A61K 7/043
[52] U.S. Cl. ........................... 424/61; 424/401
[58] Field of Search ........................ 424/61, 401

[56] References Cited

U.S. PATENT DOCUMENTS

| | | | |
|---|---|---|---|
| 3,260,637 | 7/1966 | von Bramer | 156/314 |
| 3,839,065 | 10/1974 | Overhults et al. | 106/481 |
| 4,038,345 | 7/1977 | O'Sullivan et al. | 525/284 |
| 4,042,442 | 8/1977 | Dombroski et al. | 156/310 |
| 4,102,945 | 7/1978 | Gleave | 525/293 |
| 4,105,715 | 8/1978 | Gleave | 525/276 |
| 4,215,173 | 7/1980 | Hubbard | 428/331 |
| 4,222,399 | 9/1980 | Ionescu | 132/73 |
| 4,378,213 | 3/1983 | Severy | 433/213 |
| 4,405,750 | 9/1983 | Nakata et al. | 524/717 |
| 4,626,428 | 12/1986 | Weisberg et al. | 424/61 |
| 4,646,765 | 3/1987 | Cooper | 132/73 |
| 4,669,491 | 6/1987 | Weisberg et al. | 132/73 |
| 4,687,827 | 8/1987 | Russo | 427/340 |
| 4,844,102 | 7/1989 | Repensek et al. | 132/73 |
| 4,980,086 | 12/1990 | Hiraiwa et al. | 252/511 |
| 5,059,656 | 10/1991 | Tsuji | 525/155 |
| 5,127,414 | 7/1992 | Mast et al. | 132/73 |
| 5,306,490 | 4/1994 | Barley, Jr. | 424/78.35 |
| 5,319,011 | 6/1994 | Schoon | 524/261 |
| 5,357,985 | 10/1994 | InDelicato et al. | 132/200 |
| 5,393,826 | 2/1995 | Huver et al. | 524/722 |
| 5,403,591 | 4/1995 | Tighe et al. | 424/445 |
| 5,407,666 | 4/1995 | Patel et al. | 424/61 |
| 5,428,115 | 6/1995 | Huver et al. | 525/379 |

*Primary Examiner*—John C. Bleutge
*Assistant Examiner*—Robert H. Harrison

[57] ABSTRACT

The present invention provides an improved activator and method of utilizing same in applying durable protective coating on natural or artificial nails. The activator utilized for curing a gel component has a viscosity of approximately 10 to 5000 centipoise. The activator preferably includes a solvent, a polymerization initiator, and a viscosity modifying agent. The present invention also provides a method for applying a protective coating on a nail surface. The method includes the steps of applying an effective amount of adhesive on the nail surface, applying an effective amount of an activator having a viscosity of approximately 10 to 5000 centipoise on the nail surface, blending the adhesive and the activator together on the nail surface to form a blended mixture, and brushing the blended mixture over the nail surface.

11 Claims, No Drawings

COMPOSITION AND METHOD FOR APPLYING PROTECTIVE COATING ON A NAIL SURFACE

BACKGROUND OF THE INVENTION

The present invention relates generally to nail care products and processes of applying same. More specifically, the present invention relates to compositions and processes for applying strong protective coatings to nails with or without artificial extensions to the nails.

Numerous techniques for applying protective coatings for nails, with or without extensions to the nails, exist today. The types of artificial nails produced by these techniques can be classified as: (1) glue-on nails; (2) nail wraps; (3) sculptured nails; and (4) nail dips.

In addition to these techniques, one of the most successful and popular nail systems for repair and cosmetic enhancement of nails employs a cyanoacrylate gel as an adhesive. In this "gel" method, a viscous cyanoacrylate gel itself is used as a filler or coating on a nail surface. The cyanoacrylate glue is spread over the surface of the nail or over an artificial nail already attached to the natural nail and cured to form a protective coating. Such systems have been developed that utilize a blended mixture of powders and liquids that is applied to the nail surface, as with the nail dipping method. Alternatively, cyanoacrylate liquids or gels that are applied to the nail surface with a brush or spreader are used. Separate accelerators or hardeners to cure the gel are then applied by spraying or brushing the hardener onto the previously applied layer of cyanoacrylate gel.

Specifically, in such a procedure, the artificial nail is originally glued onto the tip of the natural nail by use of a cyanoacrylate glue. The glue can also go directly over the natural nail. Once strong bonding is effected, the entire surface of the artificial and/or natural nail is coated with a viscous cyanoacrylate adhesive (commonly called gel).

This coating is accomplished in a three step process. Initially, the adhesive is applied to the nail surface by a spreading technique. Second, a solvent solution with activator, such as dimethyl-para-toluidine, is either brushed across the adhesive or sprayed and evaporates at room temperature. The product is then buffed to smooth. This results in a fairly hard, coated nail that can be polished.

However, this procedure suffers from the drawback that the polymerization of the cyanoacrylate can be quite exothermic, and depending on the amount of promoter applied, quite high temperatures can be realized on the surface of the nail. These temperatures can cause great discomfort for the user. Moreover, the finished nail may not be very strong and have a tendency to crack easily.

Still further, after the coating is applied to the nail surface, a user often applies nail polish on the nail. This additional step of polishing the nails further protracts the time required of the user to obtain beautiful colored nails. Nevertheless, to maintain beautiful colored nails, the user is forced to repeatedly apply nail polish on the nail surface.

Accordingly, a need exists for a system and method for applying a protective coating to a nail that will overcome the drawbacks of prior systems.

SUMMARY OF THE INVENTION

The present invention provides an unique activator for use in applying an artificial nail coating to a nail surface. Moreover, the present invention provides a quick, two-step method of applying an artificial nail coating that overcomes the problems of thin (non-viscous) spray or brush applied initiators of the prior art. The present invention utilizes a blended mixture of adhesive (i.e. cyanoacrylate gel) and a thickened, polymer enhanced activator to provide a safe and easy method of applying protective coating to a nail surface.

The present invention provides an activator for applying a gel component having a viscosity of approximately 10 to 5000 centipoise. Unlike prior activators, the activator of the present invention is a viscous, polymer thickened activator that mixes with the adhesive, thereby maintaining a high viscous blend. When brushed over the nail surface, this blend leaves a smooth finish that polymerizes (or cures) without the need for brushing or spraying an additional activator.

In an embodiment, the activator for curing a gel component comprises a solvent, a polymerization initiator, and a viscosity modifying agent. In a preferred embodiment, the polymerization initiator is an aromatic amine and the viscosity modifying agent includes at least one substantially non-reactive polymer. Suitable substantially non-reactive polymers, among others, include: nitro-cellulose esters; cellulose esters; toluene-sulfonamide-formaldehyde condensation polymers; polyesters of the diol terephthalate group; polyvinyl acetals; nylons; polycarbonates; terminated polymethacrylates; polyurethanes, and polymers or copolymers of ethyl, methyl or isobutyl methacrylates.

The present invention also provides a method for applying a protective coating to a nail surface. Initially, an effective amount of an adhesive is applied on the nail surface. An effective amount of the activator made pursuant to the present invention is placed over or under the adhesive. The two components are then mixed on the nail surface. This mixture is smoothed over the nail surface.

An advantage of the present invention is that it provides an activator that limits the magnitude of the exothermic temperature observed during the polymerization of the adhesive. As a result thereof, the user of such a system will experience a far lower temperature increase on the surface of the nail than with other initiator application methods.

Another advantage of the present invention is that the product experiences less shrinking and wrinkling due to slightly slower drying time and thickened activator.

Yet another advantage of the present invention is that the two component system can be kept off the user's cuticle. The two component system dries slowly so it can be removed from the cuticle or unwanted places before it sets.

Moreover, an advantage of the present invention is that the adhesive is dropped on the center of the nail and never applied full strength near the cuticle. Instead, only the blended mixture of the present invention covers the complete nail surface, resulting again in a safer and easier to use product.

Yet another advantage of the present invention is that it provides an improved activator for use in curing a gel component. In this regard, the thickened activator creates a self-leveling effect on the surface of the nail. The viscous nature of the activator and the adhesive promotes smooth spreading of the mixture, unlike prior systems.

Still further, an advantage of the present invention is that it provides an activator that can be colored. The resulting colored activator, in effect, may act as a substitute for nail polish. Naturally, eliminating the need for nail polish provides numerous economic as well as use advantages to the nail care customer.

Moreover, another advantage of the present invention is that the uses of the composition expand broader than just the nail care industry. For example, the composition may be utilized in the hobby and crafts industry.

Additional features and advantages of the present invention are described in, and will be apparent from, the detailed description of the preferred embodiments.

DETAILED DESCRIPTION OF THE PRESENTLY PREFERRED EMBODIMENTS

The present invention provides an improved method and activator for creating a smooth durable overlay over a nail surface. The present invention can be utilized directly over natural nails or with a natural nail extended with a plastic nail tip. Naturally, when the present invention is utilized as a coating over artificial nails, such artificial nails must first be adhesively bonded to the natural nail.

While the description of the present application focuses on the use of the composition in the nail care industry, the inventor believes the composition may also be utilized as a suitable adhesive mixture in other areas. For instance, the inventor believes the composition may be used in the expansive hobby and craft industry. In this regard, since the composition can be colored, in an embodiment, it may be utilized as a colored adhesive for model figures and the like. Thus, as one skilled in the art will recognize, such other uses of the composition fall within the spirit and scope of the present invention.

With respect to the use on nails, pursuant to the method of the present invention, an effective amount of an adhesive is initially applied onto the nail surface. As used herein, the term nail refers to and is intended to encompass fingernail, toenail, or other like surfaces. Naturally, with regard to viscosity, clarity and setting time, the formulas for a suitable adhesive, such as cyanoacrylate gel, will vary from manufacturer to manufacturer. While a variety of adhesives may be used in the present invention, preferably a viscous cyanoacrylate gel is applied directly on the surface of the artificial/natural nail. This adhesive should be rather viscous so as not to run over the surface of the nail.

In an embodiment, the adhesive has a viscosity ranging from approximately 1000 to 5000 centipoise. In a preferred embodiment, the adhesive has a viscosity ranging from approximately 1500–2500 centipoise.

Next, an effective amount of an activator made pursuant to the present invention is applied over the nail surface. Due to the unique application and formulation of the present invention, the activator may be applied either before or after the adhesive component. In a preferred embodiment, the activator is applied to the nail surface after the adhesive to achieve better adhesion and control of the two components on the nail surface.

Unlike prior systems, the activator of the present invention has a viscosity of approximately 10 to 5000 centipoise. Preferably, the viscosity of the activator is selected such that it maximizes the efficiency of the activator and adhesive in combination. One or more polymers and/or copolymers are dissolved in the activator to increase the viscosity similar to that of nail polishes. In an embodiment, the activator has a viscosity of approximately 100 to 3000 centipoise. In a preferred embodiment, the activator has a viscosity of approximately 500 to 2500 centipoise.

The viscous, polymer thickened activator mixes with the adhesive, maintaining a high viscous blend. When brushed over the nail surface, such blend leaves a smooth finish that polymerizes (or cures) without the need for brushing or spraying any additional activator. This method eliminates the heat caused by other activators that are sprayed or brushed on the nail. The two components of the present invention are blended together on the surface of the nail before smoothing, creating a slightly slower cure that results in more application time and control. Moreover, the method of the present invention diminishes the shrinking and wrinkling of the adhesive that usually occurs in prior art systems.

The activator of the present invention preferably includes a solvent, a polymerization initiator, and a viscosity modifying agent. Since the thickened activator is used for smoothing, spreading and polymerizing the adhesive, virtually any solvent for the adhesive (i.e. cyanoacrylate) capable of being thickened with any polymer or copolymer can be used as long as it is chosen from materials that are free of health hazards. For example, suitable solvents that may be used in the activator component include, among others, ethyl acetate, methyl acetate, butyl acetate, acetone, methylethyl ketone (MEK), and glycol esters.

The polymerization initiator, as used herein, refers to a compound capable of polymerizing the adhesive. Similar to the chemical solvent, a polymerization initiator should be selected such that it does not pose a health risk to the user. In an embodiment, the polymerization initiator is an aromatic amine. Suitable aromatic amines that may be used pursuant to the present invention include: N,N,-dimethyl-p-toluidine (DMPT); diethyl-p-toluidine; dihydroxyethyl-p-toluidine (DHEPT) and dihydroxypropyl-p-toluidine (DHPPT).

Still further, the activator of the present invention includes a viscosity modifying agent. The viscosity modifying agent refers to a polymer or the like that may be utilized to thicken the activator component. A variety of polymers may be utilized as the viscosity modifying agent to thicken the activator. Preferably, the viscosity modifying agent includes at least one substantially non-reactive polymer, which refers to a non-reactive polymer or a polymer that reacts only slightly with the other components of the activator system. Suitable substantially non-reactive polymers include, among others: nitro-cellulose esters; cellulose esters; toluene-sulfonamide-formaldehyde condensation polymers; polyesters of the diol terephthalate group; polyvinyl acetals; nylons; polycarbonates; terminated polymethacrylates; polyurethanes; and polymers or copolymers of ethyl, methyl or isobutyl methacrylates.

The unique ingredients of the claimed invention provide a thickened activator possessing many advantages. For example, thickening the activator and mixing it with the adhesive before spreading results in a smoother and stronger finish on the nail surface. The thickened activator also fills in the ridges of the nail tip better than prior systems. It also results in more application time, allowing the user to achieve a better finish on the nail surface. Due to its thickness, the activator will not run over the nail surface. Still further, the adhesive and activator in combination are easier and safer to control and do not cause excessive heat on the nail surface. Since the activator of the present invention has increased viscosity, no wet solvents are present to create a runny, unsafe product.

Moreover, the unique thickened activator of the present invention can be colored. Utilizing a colored activator eliminates the need for nail polish. Moreover, when the nail is subsequently buffed, the color will not be buffed away, unlike nail polishes. To assure a smooth finish, the colored activator is preferably applied to the nail with a brush.

A variety of dyes may be utilized to color the activator. For example, suitable coloring dyes that may be utilized pursuant to the present invention include: various types of lakes; titanium dioxide; and soluble dyes. In a preferred embodiment, the activator includes a blend of lakes and dioxides that can be obtained from Kirker Chemical located in Paterson, N.J.

The activator mixture of the present invention may also include a flow additive.

After the activator is applied to the nail surface, the adhesive and the activator are blended together on the nail surface to form a blended mixture. Because the activator stays viscous during the application process, the blended mixture exhibits more control, and therefore helps to avoid contact with surrounding skin. The preferred application is dropping both the activator and adhesive onto the surface of the nail and then mixing together with a clean brush. However, as one skilled in the art will recognize, any other means, such as using a spatula, rod, spreader or the like, can be used as long as the user maintains control for smoothing and spreading in the precise location desired.

The blended mixture is then brushed like polish over the nail surface. The thickened composite will have a tendency to self-level and smooth out over the surface. Then, after fully dried, the hardened surface can be buffed to a smooth finish and ready to polish if desired. Advantageously, careful application of the two-component system of the present invention eliminates the need to buff the nail surface. Moreover, use of the colored activator of the present invention effectively eliminates the additional step of nail polishing.

By way of example, and not limitation, examples of the activator made pursuant to the present invention will now be given.

EXAMPLES

The activator consists of parts A and B. Part A includes the solvent and the polymerization initiator; where as, part B includes the viscosity modifying agent. The following description sets forth the key components and ranges of same in the two part activator component.

| Part A | |
|---|---|
| Components | Usable Range Vol % |
| Ethyl Acetate | 0 to 100 |
| Methyl Acetate | 0 to 100 |
| Butyl Acetate | 0 to 70 |
| Dibutyl Phthalate | 0 to 10 |
| Aromatic Amine | .0001 to 6 |

Part B is one or more polymers that are used for the purpose of increasing viscosity. It is added to part A in the proportion of approximately 1 to 80 g per 100 ml. Classes of polymers suitable for this application include, among others, nitro-cellulose esters, cellulose esters, toluene-sulfonamide-formaldehyde condensation polymers, polyesters of the diol terephthalate group, polyvinyl acetates especially polyvinyl butyrol, nylons, polycarbonates, terminated polymethacrylates, polyurethanes and polymers or copolymers of ethyl, methyl or isobutyl methacrylates. Molecular weight ranges should be selected such that the polymers are soluble in the activator but still have strength properties equal to or greater than the cured part A.

As one skilled will recognize, the selection of a specific activator directly depends on the particular adhesive used. An activator should be selected such that it maximizes the efficiency of both components. Although a variety of combinations of specific chemicals may be utilized pursuant to the present invention, Example 1 below has been found to produce the best results. Such a combination produces good results with regard to smoothness, ease of final buffing, if necessary, flexibility, shine and adhesion. In this regard, preferred polymers used for part B are cellulose ester or a copolymer sold on the market as Rohmamere Plex 6639F by Rohm Tech Inc. located in Malden, Mass. Moreover, the best results have been obtained when an activator made in accordance with Example 1 is used with a cyanoacrylate gel having a viscosity of approximately 1500 to 2500 centipoise.

| Components | Volume % |
|---|---|
| Example 1 | |
| Ethyl Acetate | 30 to 95 |
| Butyl Acetate | 5 to 50 |
| Aromatic Amine | .0005 to 5 |
| Part B - 1 to 70 g per 100 ml of Part A | |
| Example 2 | |
| Ethyl Acetate | 25 to 65 |
| Methyl Acetate | 25 to 65 |
| Butyl Acetate | 5 to 50 |
| Aromatic Amine | .0005 to 5 |
| Part B - 5 to 55 g per 100 ml Part A | |
| Example 3 | |
| Methyl Acetate | 30 to 95 |
| Butyl Acetate | 5 to 50 |
| Aromatic Amine | .0005 to 5 |
| Part B - 5 to 55 g per 100 ml Part A | |
| Example 4 | |
| Ethyl Acetate | 25 to 65 |
| Methyl Acetate | 25 to 65 |
| Butyl Acetate | 5 to 50 |
| Aromatic Amine | .0005 to 5 |
| Dibutyl Phthalate | .005 to 5 |
| Part B - 5 to 55 g per 100 ml Part A | |
| Example 5 | |
| Methyl Acetate | 30 to 95 |
| Butyl Acetate | 5 to 50 |
| Aromatic Amine | .0005 to 5 |
| Dibutyl Phthalate | .005 to 5 |
| Part B - 5 to 55 g per 100 ml Part A | |
| Example 6 | |
| Ethyl Acetate | 30 to 95 |
| Butyl Acetate | 5 to 50 |
| Dibutyl Phthalate | .005 to 5 |
| Aromatic Amine | .0005 to 5 |
| Part B - 1 to 70 g per 100 ml Part A | |
| Example 7 | |
| Ethyl Acetate | 70 to 99 |
| Aromatic Amine | .0005 to 5 |
| Part B - 1 to 70 g per 100 ml Part A | |
| Example 8 | |
| Methyl Acetate | 70 to 99 |
| Aromatic Amine | .0005 to 5 |
| Part B - 1 to 70 g per 100 ml Part A | |
| Example 9 | |
| Ethyl Acetate | 70 to 99 |
| Aromatic Amine | .0005 to 5 |

-continued

| Components | Volume % |
|---|---|
| Dibutyl Phthalate | .005 to 5 |
| Part B - 5 to 55 g Per 100 ml Part A | |

Example 10

| | |
|---|---|
| Methyl Acetate | 70 to 99 |
| Aromatic Amine | .0005 to 5 |
| Dibutyl Phthalate | .005 to 5 |
| Part B - 5 to 55 g per 100 ml Part A | |

By way of example, and not limitation, a preferred example of applying the protective coating of the present invention to a nail surface will now be given.

A nail (natural or nail tip extension) is gently buffed. One drop (or more depending on nail surface and length) of a cyanoacrylate gel is placed on the center of the nail to be covered. A drop(s) of the thickened activator is then applied on the nail surface. The two components are then mixed together carefully on the nail surface with a clean brush or other suitable spreader. The mixed ingredients are then brushed over the nail surface like nail polish until the mixture becomes slightly stringy, indicating it is starting to set. The brush is removed and the mixture levels slightly as it continues to polymerize and dry.

Understandably, various changes and modifications to the presently preferred embodiments described herein will be apparent to those skilled in the art. Such changes and modifications can be made without departing from the spirit and scope of the present invention and without diminishing its attendant advantages. Therefore, the appended claims are intended to cover such changes and modifications.

I claim:

1. An activator for curing a gel component comprising a premixed composition of:
   a solvent selected from the group consisting of ethyl acetate, methyl acetate, butyl acetate, methyl ethyl ketone, glycol esters and dibutyl phthalate;
   a polymerization initiator; and
   a viscosity modifying agent comprising at least one substantially non-reactive polymer, the premixed composition being mixed together prior to combination with the gel component.

2. The activator of claim 1 wherein the polymerization initiator is an aromatic amine.

3. The activator of claim 2 wherein the aromatic amine is selected from the group consisting of: N,N-dimethyl-p-toluidine; diethyl-p-toluidine; dihydroxyethyl-p-toluidine; and dihydroxypropyl-p-toluidine.

4. The activator of claim 1 wherein the viscosity modifying agent is selected from the group consisting of: nitrocellulose esters; cellulose esters; toluene-sulfonamide-formaldehyde condensation polymers; polyesters of the diol terephthalate group; polyvinyl acetals; nylons; polycarbonates; terminated polymethacrylates; polyurethanes; and polymers or copolymers of ethyl, methyl or isobutyl methacrylates.

5. The activator of claim 1 including a coloring dye.

6. An activator adapted for admixture with a curable gel component comprising a premixed composition of:
   a solvent selected from the group consisting of ethyl acetate, methyl acetate, butyl acetate, methyl ethyl ketone, glycol esters and dibutyl phthalate;
   a polymerization initiator; and
   a viscosity modifying agent comprising at least one substantially non-reactive polymer, the activator having a viscosity of approximately 10 to 5000 centipoise.

7. The activator of claim 6 wherein the polymerization initiator is an aromatic amine.

8. The activator of claim 7 wherein the aromatic amine is selected from the group consisting of: N,N-dimethyl-p-toluidine; diethyl-p-toluidine; dihydroxyethyl-p-toluidine; and dihydroxypropyl-p-toluidine.

9. The activator of claim 6 wherein the viscosity modifying agent is selected from the group consisting of: nitrocellulose esters; cellulose esters; toluene-sulfonamide-formaldehyde condensation polymers; polyesters of the diol terephthalate group; polyvinyl acetals; nylons; polycarbonates; terminated polymethacrylates; polyurethanes; and polymers or copolymers of ethyl, methyl or isobutyl methacrylates.

10. The activator of claim 6 further including a coloring dye.

11. An activator for curing a gel component comprising a premised composition of:
   a solvent capable of dissolving the gel component;
   a polymerization initiator; and
   a viscosity modifying agent comprising at least one substantially non-reactive polymer, the activator comprising parts A and B, wherein part A comprises:
   approximately 5 to 50 vol % of butyl acetate;
   approximately 0.0005 to 5 vol % of an aromatic amine; and
   part B comprises the substantially non-reactive polymer present in a range of approximately 1 to 70 grams per 100 ml of part A.

* * * * *